United States Patent [19]
Nguyen et al.

[11] Patent Number: 5,932,608
[45] Date of Patent: Aug. 3, 1999

[54] MELATONIN DERIVATIVE DERMOCOSMETIC COMPOSITIONS FOR WHITENING/DEPIGMENTING THE SKIN

[75] Inventors: Quang Lan Nguyen, Antony; Jean-François Nadaud, Clamart, both of France

[73] Assignee: Societe L'Oreal S.A., Paris, France

[21] Appl. No.: 08/900,828

[22] Filed: Jul. 25, 1997

[30] Foreign Application Priority Data

Jul. 25, 1996 [FR] France .................................. 96 09388

[51] Int. Cl.$^6$ ........................ A01N 43/38; A61K 31/405; A61K 7/135; A61K 7/00
[52] U.S. Cl. .......................... 514/415; 424/62; 424/401; 424/489; 514/844; 514/845; 514/937; 514/944
[58] Field of Search .................... 424/401, 489, 424/62; 514/415, 844, 845, 937, 944

[56] References Cited

U.S. PATENT DOCUMENTS 4,746,674  5/1988  Pierpaoli et al. ........................ 514/415

FOREIGN PATENT DOCUMENTS

| | | |
|---|---|---|
| 61-221104 | 10/1986 | Japan . |
| 87/00432 | 1/1987 | WIPO . |
| 92/01810 | 2/1992 | WIPO . |

OTHER PUBLICATIONS

Patent Abstract of Japan, vol. 011, No. 060 (C–405), Feb. 24, 1987 & JP 61 221104 A.

Chemical Abstracts, vol. 82, No. 5, Feb. 5, 1975, Columbus, Ohio, abstract No. 28987.

Chemical Abstracts, vol. 85, No. 1, Jul. 5, 1976, Columbus, Ohio, abstract No. 590.

Bangha et al., "Topical melatonin (N–acetyl–5–methoxytryptamine) suppresses UV–induced erythema", The Journal of Investigative Dermatology, V106, No. 4, p. 944, Abstract No. 833, Apr. 1996.

Nordlund et al., "The effects of oral melatonin on skin color and on the release of pituitary hormones", J. Clin. Endocrinol. Metab. 45, 768–774, 1977.

Sugden, "Aggregation of pigment granules in single cultured *Xenopus laevis* melanophored by melatonin analogues", Br. J. Pharmacol., 104, 922–927, 1991.

Valverde et al., "Melatonin antagonizes alfa–melanocyte–stimulating hormone enhancement of melanogenesis in mouse melanoma cells by blocking the hormone–induced accumulation of a c locus typrosinase", Eur. J. Biochem., 232, 257–263, 1995.

*Primary Examiner*—Shelley A. Dodson
*Assistant Examiner*—Marina Lamm
*Attorney, Agent, or Firm*—Burns, Doane, Swecker & Mathis, L.L.P.

[57] ABSTRACT

Topically applicable dermocosmetic compositions for whitening/depigmenting human skin, comprise a skin-whitening/depigmenting effective amount of at least one melatonin derivative having the structural formula (I):

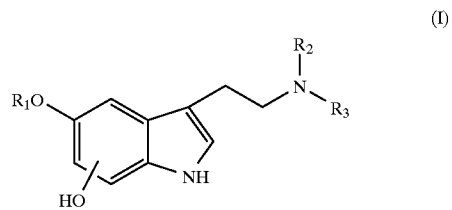

in which $R_1$ is a lower alkyl radical, $R_2$ is a hydrogen atom or a lower alkyl radical, and $R_3$ is a hydrogen atom or a lower acyl radical, with the proviso that the hydroxyl radical is in the 4-, 6- or 7-position on the indole ring system, or a physiologically acceptable salt, solvate or bioprecursor/prodrug thereof, formulated into a topically applicable, cosmetically/dermatologically acceptable vehicle, carrier or diluent therefor.

10 Claims, 2 Drawing Sheets

MELATONIN DERIVATIVE DERMOCOSMETIC COMPOSITIONS FOR WHITENING/DEPIGMENTING THE SKIN

CROSS-REFERENCE TO COMPANION APPLICATIONS

Copending applications Ser. No. 08/900,109 and Ser. No. 08/900,832, each filed concurrently herewith and each assigned to the assignee hereof.

BACKGROUND OF THE INVENTION

1. Technical Field of the Invention

The present invention relates to novel topically applicable dermocosmetic compositions comprising certain melatonin derivative depigmenting agents, for treating the skin of the face and/or the body, for the purpose of whitening the skin or for treating pigmentation blemishes.

2. Description of the Prior Art

At different periods in their lifetimes, certain individuals develop dark and/or colored blemishes on the skin and, more especially, on the hands, imparting to the skin a heterogeneous appearance. These blemishes are due to a considerable concentration of melanin in the keratinocytes located at the skin surface. The reason for this is that the melanocytes located deep in the epidermis produce melanin and deliver such melanin to the surrounding kertinocytes, which then rise to the surface of the epidermis, loaded with melanin.

The mechanism of formation of skin pigmentation, namely, the formation of melanin, is particularly complex and schematically includes the following principal mechanisms:

Tyrosine→Dopa→Dopaquinone→Dopachrome→Melanin

Tyrosinase is the essential enzyme involved in this reaction sequence. In particular, it catalyzes the reaction for the conversion of tyrosine into dopa (dihydroxyphenylalanine) and the reaction for the conversion of dopa into dopaquinone. This tyrosinase acts only when it is in a mature state, under the influence of certain biological factors.

An active species is recognized as being depigmenting if it acts directly on the vitality of the epidermal melanocytes in which melanogenesis takes place and/or if it interferes with one of the steps in the biosynthesis of melanin, either by inhibiting one of the enzymes involved in melanogenesis or by inserting itself as a structural analog of one of the chemical compounds of the synthetic chain of melanin, which chain may thus become blocked and ensure depigmentation.

The active species most commonly used as depigmenting agents are, more particularly, hydroquinone and derivatives thereof, in particular its ethers such as hydroquinone monomethyl ether and monoethyl ether. Although they exhibit a certain level of efficacy, these compounds are, unfortunately, not free of side effects taking account of their toxicity, which renders them complicated, or even dangerous, to use. This toxicity arises from the fact that they intervene in fundamental mechanisms of melanogenesis by killing cells which then present the risk of disturbing their biological environment and which consequently oblige the skin to eliminate them by producing toxins.

Thus, hydroquinone, the use of which is moreover legally limited to a concentration of 2%, is a compound which is particularly irritant and cytotoxic to melanocytes, and the total or partial replacement of which thus constitutes a desideratum in this art.

The application of harmless topical depigmenting substances which are of good efficacy is most particularly desired in order to treat regional hyperpigmentations caused by melanocyte hyperactivity, such as idiopathic melasmas which occur over the course of pregnancy ("pregnancy mask" or chloasma), or of estroprogestative contraception, localized hyperpigmentations caused by benign melanocyte proliferation and hyperactivity, such as senile pigmentation blemishes deemed actinic lentigo, accidental hyperpigmentations such as post-lesional cicatrization and photosensitization, as well as certain leucodermias such as vitiligo. For the latter hyperpigmentations, failing being able to repigment the damage to the skin, it is possible to depigment the areas of residual normal skin in order to provide the skin, as a whole, with a homogeneous white complexion.

2,5-Dihydroxyphenylcarboxylic acid derivatives or benzofuran derivatives are described for such purpose in EP-0,524,108 and EP-0,526,302.

SUMMARY OF THE INVENTION

It has now unexpectedly been determined that certain melatonin derivatives are effective for treating skin blemishes and pigmentation.

Melatonin, or N-acetyl-5-methoxytryptamine, is especially known for its circadian activity in regulating the production of hormones, in particular for its influence on the rhythm of sleep. It has also been described for its antioxidant activity and for formulation into dermocosmetics for improving the appearance of the skin (JP-61/221,104; U.S. Pat. No. 4,746,674) or for protecting the skin against the deleterious effects of irradiation with UV rays (EP 0,438, 856; E. Bangha et al., *Dermatology*, 191, [2], 176 (1995)). Various topical compositions comprising melatonin for therapeutic or cosmetic usage have been described, such as cleansing lotions and cleansing creams or milks (JP-61/221,104).

Although melatonin can modify the production of A-MSH at the central level, and consequently the production of melanin, the literature suggests that exogenous melatonin has no effect on skin pigmentation in man (D. B. McElhinney et al., *J. Invest. Dermatol*, 102 (2), 258–9 (1994)).

Briefly, the present invention features topically applicable dermocosmetic compositions comprising skin whitening/depigmenting amounts of at least one melatonin derivative having the structural formula (I):

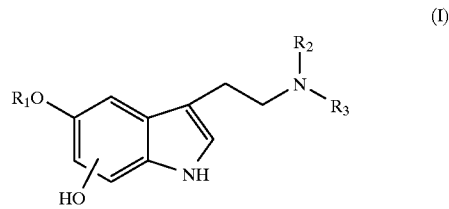

in which $R_1$ is a lower alkyl radical, $R_2$ is a hydrogen atom or a lower alkyl radical, and $R_3$ is a hydrogen atom or a lower acyl radical, with the proviso that the hydroxyl radical on the indole ring system is in the 4-, 6- or 7-position or its physiologically acceptable salts, solvates or bioprecursors.

Figure 1:
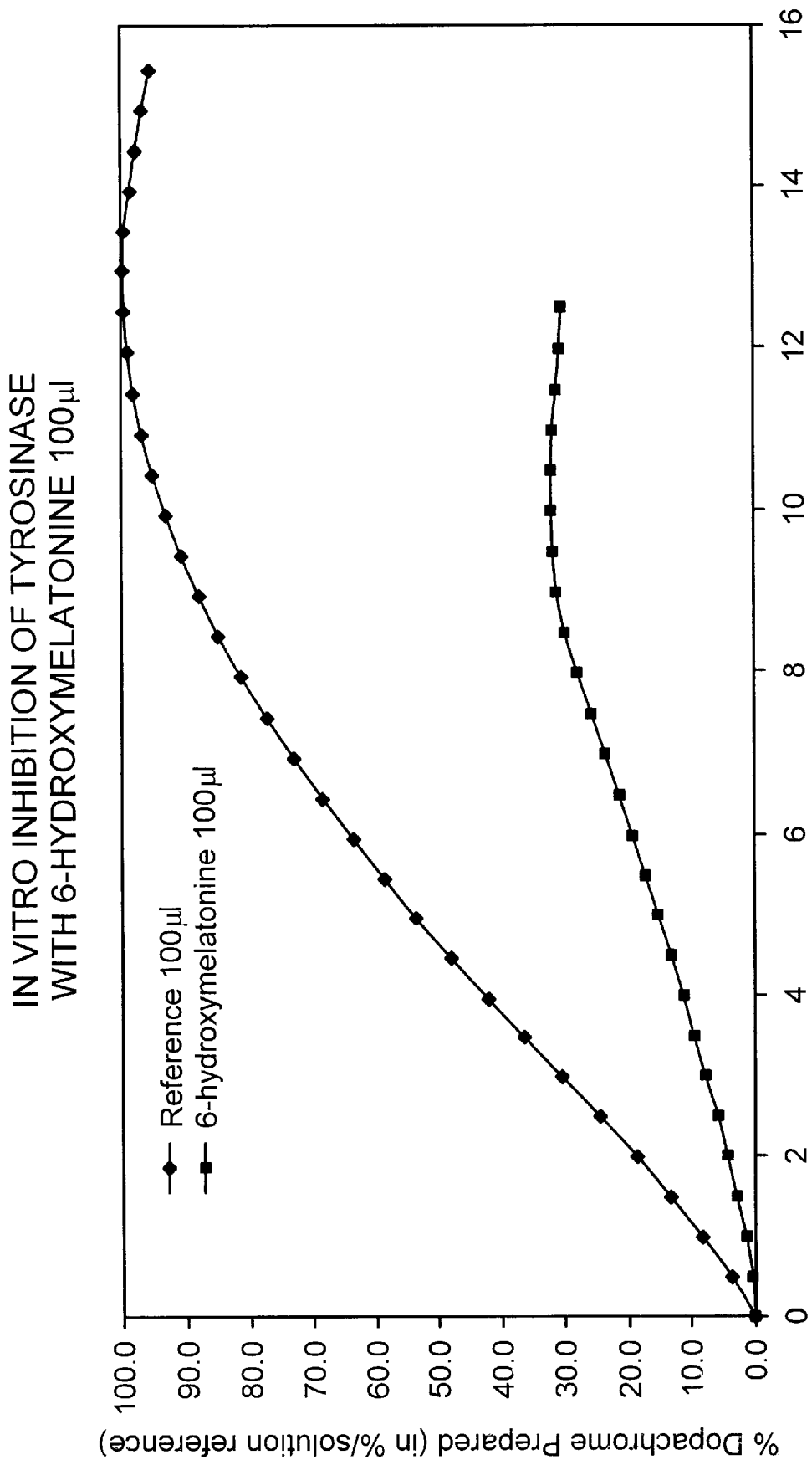
FIGS. 1 and 2 are graphs plotting inhibition of tyrosinase over time, i.e., percentage of formation of dopachrome, both in the presence and absence of a dermocosmetic composition according to the invention.

DETAILED DESCRIPTION OF BEST MODE AND SPECIFIC/PREFERRED EMBODIMENTS OF THE INVENTION

More particularly according to the present invention, the subject melatonin derivatives advantageously have the structural formula (Ia):

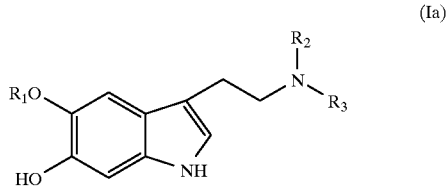

(Ia)

in which $R_1$, $R_2$ and $R_3$ are as defined above and the hydroxyl radical is in position 6.

By the term "lower alkyl" is preferably intended a linear or branched $C_1$ to $C_4$ alkyl radical, optionally substituted with one or more halogen atoms (F, Cl or Br). These are, in particular, methyl, ethyl, propyl or butyl radicals. This definition also applies to the alkyl moieties of the acyl radicals.

By the term "salt" is intended any addition salt of a physiologically acceptable inorganic or organic acid, which is common for cosmetically or dermatologically active compounds, such as addition salts with hydrochloric acid, sulfuric acid, acetic acid, citric acid, fumaric acid, hemisuccinic acid, maleic acid, and the like.

By the term "physiologically acceptable bioprecursor" is intended any derivative or prodrug capable of liberating the compounds of general formula (I) above once they have been administered, in particular the esters, such as alkyl phosphates, alkyl sulfates or acyls (for example acetate), or monosaccharides (in particular glucosyl, mannosyl, fructosyl, N-acetylglucamine or galactosyl) of the hydroxyl radical.

The melatonin derivatives comprising the compositions of the present invention preferably constitute from 0.0001% to 10% by weight and even more preferably from 0.001% to 1% by weight thereof.

Topical application of a composition containing a melatonin derivative according to the invention makes it possible to obtain a marked decrease or even total disappearance of the formation of pigmentation blemishes. Without wishing to be bound to any particular theory, the mechanism of action of the melatonin derivatives appears to dictate that the depigmentation is obtained by the application of a suitable amount of melatonin derivative which is sufficient to inhibit the tyrosinase of skin melanocytes.

Thus, the present invention features a regimen for the cosmetic treatment of skin pigmentation blemishes, comprising topically applying to the skin a composition containing, as a skin depigmenting agent, an effective amount of a melatonin derivative of formula (I) as defined above.

The present invention also features a cosmetic treatment or regimen for inhibiting the tyrosinase of skin melanocytes, which comprises topically applying an effective amount of a melatonin derivative of formula (I) to the skin.

Too, the present invention features dermocosmetic depigmenting compositions comprising a topically applicable, cosmetically or dermatologically acceptable support (vehicle, diluent or carrier) and, as the depigmenting agent therefor, an effective amount of a melatonin derivative as described above.

The dermocosmetic compositions containing the melatonin derivatives according to the invention may exist in any pharmaceutical form normally employed for topical application, for example in the form of aqueous, aqueous/alcoholic or oily solutions, dispersions of the lotion or serum type, aqueous, anhydrous or oily gels, emulsions of liquid or semi-liquid consistency of the milk type, which are obtained by dispersing a fatty phase in an aqueous phase (O/W) or, conversely, (W/O), or suspensions or emulsions of soft, semi-solid or solid consistency of the cream or gel type, or, alternatively, microemulsions, microcapsules, microparticles or vesicle dispersions of ionic and/or nonionic type. These compositions are formulated via the usual techniques.

In known manner, the cosmetic or dermatological compositions of the invention may also contain additives and adjuvants that are common in the cosmetic or dermatological arts, such as emulsifiers, hydrophilic or lipophilic gelling agents, hydrophilic or lipophilic active agents, preservatives, antioxidants, biologically active agents, fragrances, fillers, odor-absorbers, screening agents and dyestuffs and colorants. The amounts of these various additives and adjuvants are those conventionally used in the cosmetic and/or dermatological fields and, for example, constitute from 0.01% to 20% of the total weight of the composition. Depending on their nature, these additives and adjuvants may be introduced into the fatty phase, into the aqueous phase and/or into the lipid vesicles.

Water-in-oil (W/O) or oil-in-water (O/W) emulsifiers may be employed as emulsifiers, depending on the final emulsion desired.

Exemplary emulsifiers include PEG-20 stearate, PEG-100 stearate, polysorbate 60 (Tween 60 marketed by ICI), sorbitan stearate (Span 60 marketed by ICI) and PPG-3 myristyl ether.

The emulsifier content advantageously ranges from 0.1% to 15% by weight and preferably from 0.5% to 5% by weight relative to the total weight of the composition.

Co-emulsifiers may be formulated into the compositions according to the invention, for example in an amount ranging from 0.05% to 10% by weight relative to the total weight of the composition. Glyceryl stearate is a representative co-emulsifier.

In the lipid vesicle dispersions, the emulsifier may comprise ionic and/or nonionic lipid vesicles.

Exemplary oils which may be incorporated into the compositions of the invention include mineral oils, plant oils (sunflower oil, apricot kernel oil or karite butter), synthetic oils, silicone oils (cyclomethicone) and fluoro oils (perfluoropolyethers). Fatty alcohols (stearyl alcohol), fatty acids (stearic acid) and waxes may be added to these oils.

Exemplary hydrophilic gelling agents include carboxyvinyl polymers, glyceryl polyacrylates or polymethacrylates, polyacrylamides, natural gums (xanthan) and clays, and, representative lipophilic gelling agents include the modified clays such as bentones, metal salts of fatty acids such as aluminum stearates, and hydrophobic silica.

Proteins or protein hydrolysates, amino acids, polyols, in particular glycerol or sorbitol, urea, allantoin, sugars and derivatives thereof, and glycyrrhetinic acid are exemplary hydrophilic active agents.

Representatie lipophilic active agents include tocopherol (vitamin E) and derivatives thereof, essential fatty acids, ceramides and essential oils.

And exemplary UV screening agents of lipophilic or hydrophilic nature that may be formulated into the subject compositions include the titanium oxides and zinc oxides.

The subject compositions, in particular, constitute protective, treatment or care creams for the face, for the hands or for the body, protective or care milks for the body, skincare or skin treatment lotions, ointments, gels or mousses, cleansing or disinfecting lotions, compositions for the bath, foundations and tinted creams. In the latter instance, the composition contains pigments.

In order to further illustrate the present invention and the advantages thereof, the following specific examples are given, it being understood that same are intended only as illustrative and in nowise limitative.

EXAMPLE 1

In vitro activity:

The activity of the derivatives according to the invention as depigmenting agents was demonstrated in the in vitro test of inhibition of tyrosinase.

According to this test, the amount of dopachrome formed during the reaction sequence for the conversion of tyrosine into melanins was monitored by visible spectrometry at 475 nm. These reactions were catalyzed in vitro by fungal tyrosinase, in the presence of a reductive co-substrate (for example L-dopa in small amounts) in order to initiate the hydroxylation reaction of the L-tyrosine into L-dopa, which was then oxidized catalytically into dopaquinone and then into dopachrome.

The concentration of dopachrome formed over time was thus measured in the presence and absence of the inhibitor. The inhibition effect is expressed by lowering the maximum amount of dopachrome formed (optical density value at 475 nm read at the plateau of the curve) relative to the amount obtained in the absence of inhibitor.

Reactants

A. 0.1M phosphate buffer pH 6.5 (1% Tween 20)

B. Stock solution of $2 \times 10^{-3}$M L-tyrosine in A

C. Stock solution of $10^{-4}$M L-dopa in A

D. Stock solution of fungal tyrosinase containing 2400 units/ml in A

E. Stock solution of the inhibitor at $10^{-2}$M in A

The solutions C and D were prepared on the day of use.
Results
Reference cell: 3 ml of A
Test cell: 1 ml of B
0.1 ml of C
1.85 ml of A+E
Homogenize and equilibrate at 25° C.
add 0.05 ml of D Mixed together rapidly and observed the kinetics by measuring the absorbance as a function of time.

Figure 2:
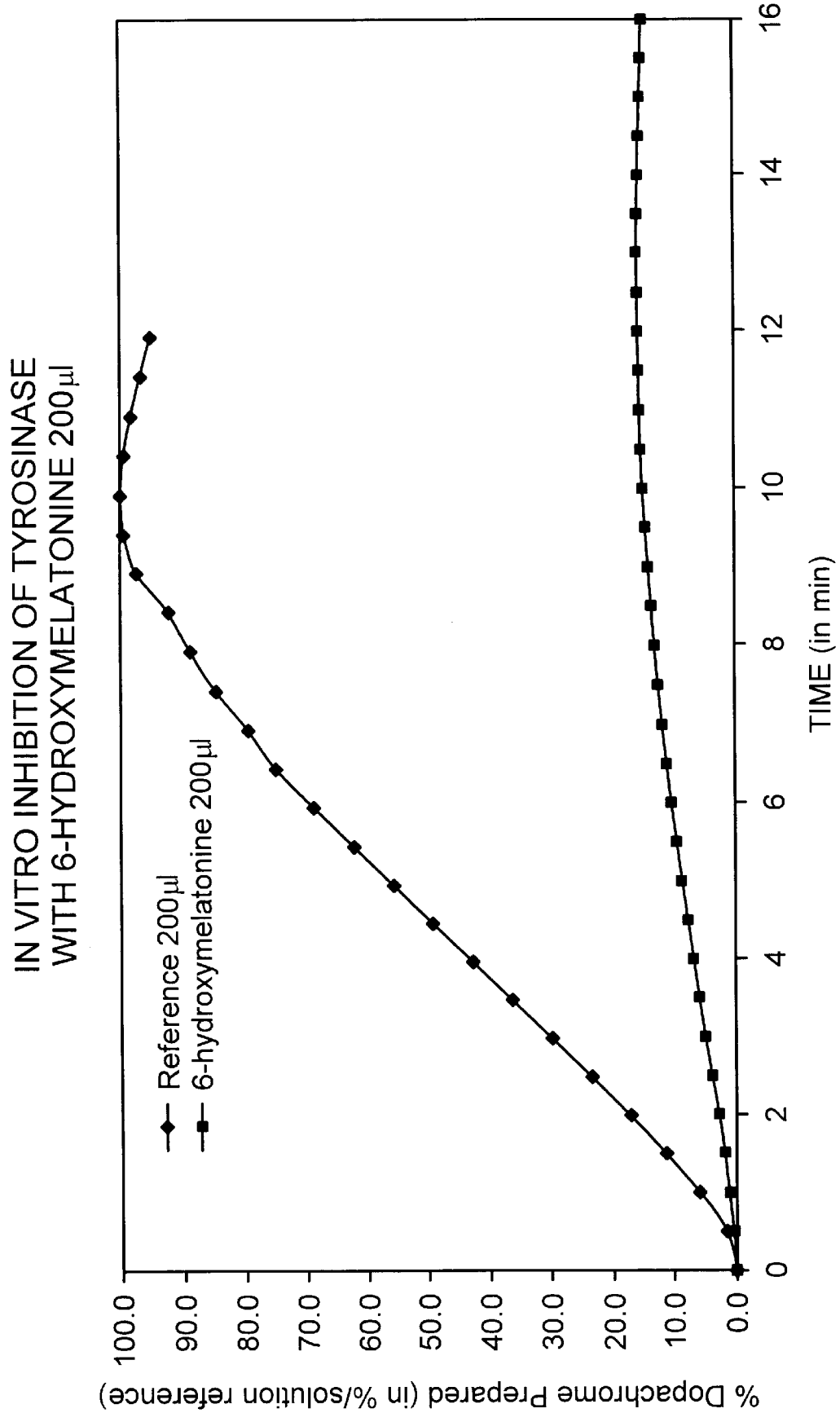

Tests were carried out with 6-hydroxymelatonin for 0.1 and 0.2 ml of solution E. The results obtained with and without 6-hydroxymelatonin are reported in the attached FIGS. 1 and 2. In both cases, a significant inhibition of the tyrosinase activity was observed by a decrease in the percentage of formation of dopachrome.

Similar tests carried out with melatonin and 5-hydroxytryptamine derivatives indicated an absence of inhibition.

Composition examples:

The following examples illustrate specific compositions according to the invention. In said compositions, the proportions indicated are percentages by weight.

EXAMPLE 2

Oil-in-water emulsion:

| | |
|---|---|
| 6-Hydroxymelatonin | 0.05% |
| Octyldodecanol | 5% |
| Sunflower oil | 11% |
| EDTA | 0.05% |
| Sodium hydroxide | 0.02% |
| Xanthan gum | 0.2% |
| Polyacrylamide/isoparaffin/laureth-7 (Sepigel 305 marketed by Seppic) | 0.9% |
| Cyclomethicone | 5% |
| Glycerol | 4% |
| Polyglyceryl acrylate at a concentration of 2% in a water/glycerol mixture (Lubrajel marketed by the Guardian) | 5% |
| Glyceryl stearate | 0.6% |
| PEG-100 stearate | 0.6% |
| PEG-20 stearate | 1.2% |
| Stearic acid | 0.6% |
| Stearyl alcohol | 1% |
| Preservatives | 0.3% |
| Water | qsp 100% |

A white fluid cream with depigmenting properties was obtained.

EXAMPLE 3

Oil-in-water emulsion:

| | |
|---|---|
| 6-Hydroxymelatonin | 0.3% |
| Apricot kernel oil | 10% |
| Karite oil | 7% |
| PPG-3 myristyl ether | 5% |
| Polysorbate 60 (Tween 60) | 2.5% |
| Sorbitan stearate (Span 60) | 2.5% |
| Preservatives | 0.2% |
| Cyclomethicone | 4% |
| Xanthan gum | 0.2% |
| Carboxyvinyl polymer | 0.5% |
| Triethanolamine (neutralizing agent) | 0.5% |
| Glycerol | 5% |
| Water | qsp 100% |

A good depigmenting day cream was obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for whitening or depigmenting human skin comprising topically applying an effective amount of a topically applicable composition for whitening/depigmenting human skin, comprising a skin-whitening/depigmenting effective amount of at least one melatonin derivative having the structural formula (I):

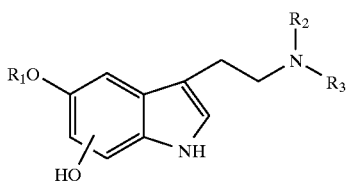

in which $R_1$ is a lower alkyl radical, $R_2$ is a hydrogen atom or a lower alkyl radical, and $R_3$ is a hydrogen atom or a lower acyl radical, with the proviso that the hydroxyl radical is in the 4-, 6- or 7-position on the indole ring system, or a physiologically acceptable salt, solvate or bioprecursor/prodrug thereof, formulated into a topically applicable, cosmetically/dermatologically acceptable vehicle, carrier or diluent therefor.

2. The method as defined by claim 1, wherein, in formula (I), the hydroxyl radical is in the 6-position.

3. The method as defined by claim 1, wherein, in formula (I), $R_1$ is a methyl radical, $R_2$ is a hydrogen atom and $R_3$ is an acetyl radical.

4. The method as defined by claim 1, wherein said at least one melatonin derivative is an ester or monosaccharide of said hydroxyl radical.

5. The method of claim 1, wherein the applied composition comprises from 0.0001% to 10% by weight of said at least one melatonin derivative.

6. The method of claim 5, wherein the applied composition comprises from 0.001% to 1% by weight of said at least one melatonin derivative.

7. The method of claim 1, wherein the applied composition is a solution, suspension, dispersion, lotion, serum, emulsion, milk, cream, gel, ointment, mousse, foundation, microcapsules, microparticles, or vesicle dispersion.

8. The method of claim 7, wherein the applied composition is an emulsion.

9. The method of claim 1, wherein the applied composition comprises at least one conventional dermatological/cosmetic additive or adjuvant.

10. A method for inhibiting the tyrosinase of human skin melanocytes, comprising topically applying to human skin a tyrosinase-inhibiting effective amount of at least one melatonin derivative having the structural formula (I):

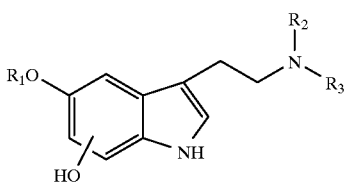

in which $R_1$ is a lower alkyl radical, $R_2$ is a hydrogen atom or a lower alkyl radical, and $R_3$ is a hydrogen atom or a lower acyl radical, with the proviso that the hydroxyl radical is in the 4-, 6- or 7-position on the indole ring system, or a physiologically acceptable salt, solvate or bioprecursor/prodrug thereof.

* * * * *